United States Patent [19]

Rigby

[11] 4,399,424
[45] Aug. 16, 1983

[54] GAS SENSOR

[75] Inventor: Leslie J. Rigby, Bishops Stortford, England

[73] Assignee: ITT Industries, Inc., New York, N.Y.

[21] Appl. No.: 308,290

[22] Filed: Oct. 5, 1981

[30] Foreign Application Priority Data

Oct. 7, 1980 [GB] United Kingdom ............. 8032248

[51] Int. Cl.³ .............................................. H01L 7/00
[52] U.S. Cl. ...................................... 338/34; 338/308; 338/309
[58] Field of Search ................... 338/34, 35, 308, 309; 73/27 R; 422/98; 29/610 R; 252/408

[56] References Cited

U.S. PATENT DOCUMENTS 3,479,257 11/1969 Shaver ............................... 338/34 X
3,901,067 8/1975 Broadman, Jr. et al. ........ 338/34 X
4,343,768 8/1982 Kimura ............................ 338/34 X Primary Examiner—C. L. Albritton
Attorney, Agent, or Firm—T. E. Kristofferson; A. D. Stolzy

[57] ABSTRACT

A semiconductor gas sensor comprises an insulating substrate (11) on which a resistive heater track (15) coupled to a pair of electrodes (12, 14) is deposited. A film (16) of a semiconductive metal oxide, typically a doped oxide, is ion-plated on to the assembly so as to contact the resistive track (15) and a further electrode (13). Exposure of the device to a particular gas, e.g. hydrogen sulphide, reduces the resistivity of the semiconductive film (16), this change being detected via an amplifier circuit (not shown). In an alternative version of the sensor (FIGS. 5a, 5b and 6) the heater is disposed under a dielectric layer, the semiconductive film being ion-plated onto the dielectric layer and electrodes therein.

3 Claims, 7 Drawing Figures

GAS SENSOR

This invention relates to semiconductor gas sensors and to methods of fabrication of such sensors.

The detection and measurement of toxic gases is an important problem in industry. Some gases, for example hydrogen sulphide, are extremely poisonous and it is therefore essential to provide a detection system that provides reliable measurement at concentrations as low as 1 to 10 parts per million. A number of detection techniques for toxic gases have been described. Analytical techniques, such as gas chromatography and absorption/titration are of course both accurate and reliable at these low concentrations but suffer from the disadvantage that the equipment involved is both bulky and delicate. Furthermore, the response time inherent in these techniques is relatively long and thus renders them unsuitable for providing a continuous series of readings. In an attempt to overcome these disadvantages semiconductor gas sensors have been developed. Sensors of this type include a thin film of a semiconductive material, typically a metal oxide, deposited on an insulating substrate. The material is such that its electrical resistance changes in the presence of traces of the toxic gas under investigation, this change in resistance being monitored via an amplifier. Whilst such devices are portable and have a relatively rapid response time they suffer from the disadvantage that present manufacturing methods produce devices with a wide range of electrical characteristics. This necessitates a relatively large investment in testing equipment and quality control.

According to one aspect of the present invention there is provided a semiconductor sensor for detecting and measuring the concentration of a gas or vapour, the sensor including a semiconductive metal oxide film ion-plated on to an insulating substrate, and wherein said oxide film is such that its resistivity is a function of the concentration of said gas or vapour adjacent the film.

According to another aspect of the invention there is provided a semiconductive sensor for detecting and measuring the concentration of a gas or vapour, the sensor including an insulating substrate, a resistive heater track disposed on the substrate, an electrode adjacent to the said heater, and an ion-plated semiconductive metal oxide film deposited at least in the region between the electrode and the heater, and wherein said oxide film is such that its resistivity is a function of the concentration of said gas or vapour adjacent the film.

According to yet another aspect of the present invention there is provided a semiconductor sensor for detecting and measuring hydrogen sulphide, the sensor comprising an alumina substrate having first, second and third electrodes disposed thereon, a substantially U-shaped resistive heater track deposited on the substrate and connected to the first and third electrodes, and an ion-plated film of alumina-doped tin oxide deposited at least in the region between the third electrode and the heater track.

According to another aspect of the present invention there is provided a semiconductor sensor for detecting and measuring the concentration of a gas or vapour, the sensor including an insulating substrate, a resistive heater strip disposed on the substrate, a dielectric layer disposed on the insulating substrate and covering the heater strip, means for electrically contacting the heater strip whereby to heat it, first and second spaced electrodes disposed on the dielectric layer in the vicinity of the heater strip, and an ion-plated semiconductive metal oxide film deposited on the dielectric layer at least in the region between the first and second electrodes, the oxide film being contacted by the first and second electrodes and being such that its resistivity is a function of a concentration of said gas or vapour adjacent the film.

According to a further aspect of the invention there is provided a method of making a semiconductive gas sensor, including depositing an electrode array on an insulating substrate, depositing a resistive heater track on the array such that the track is coupled between two electrodes of the array, and ion-plating a metal oxide film on to the substrate such that the film is disposed at least in a region between a further electrode of the array and the heater track.

According to a still further aspect of the present invention there is provided a method of making a semiconductor gas sensor, including the steps of depositing a resistive heater strip on an insulating substrate, providing a dielectric layer on the insulating substrate such as to cover the heater strip, depositing first and second spaced electrodes on the dielectric layer in the vicinity of the heater strip, and ion-plating a semi-conductive metal oxide film on the dielectric layer such that the film is disposed at least in a region between the first and second electrodes and in contact therewith.

We have found that ion-plated semiconductive layers show a high degree of uniformity and reproducibility. The technique also facilitates doping of the semi-conductive layer so that a specific response to a particular gas, typically hydrogen sulphide, is provided.

Embodiments of the invention will now be described with reference to the accompanying drawings in which.

Figure 1:
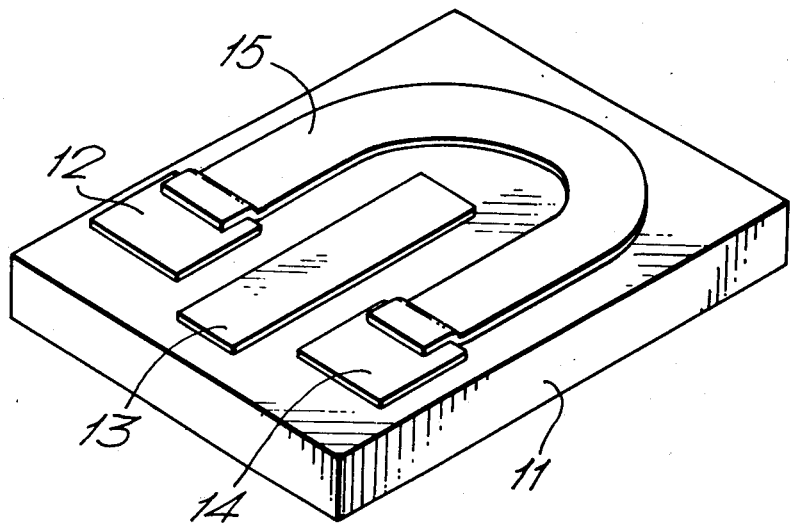
FIG. 1 is a plan view of one embodiment of a semiconductor gas sensor device.
Figure 2:
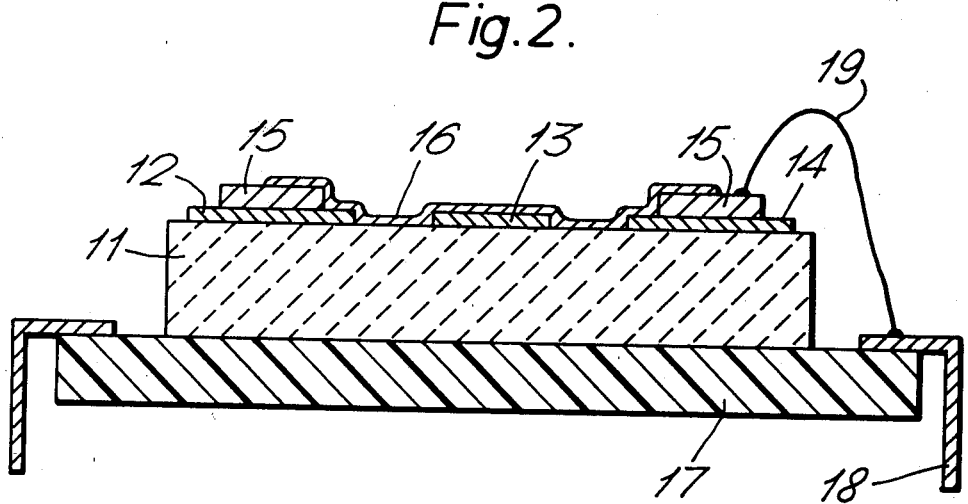
FIG. 2 is a cross-section of the device of FIG. 1.

Referring to FIGS. 1 and 2, a semiconductor gas sensor includes an insulating, typically alumina, substrate 11 on which an array of precious metal electrodes 12, 13, 14 is deposited. We prefer to employ gold or gold alloy electrodes as these materials are both chemically inert and relatively easy to apply. Typically the electrodes are formed by deposition of thick film inks followed by firing, or by vacuum evaporation. As can be seen from FIG. 1 the electrode array comprises a pair of relatively small electrodes 12, 14 with an elongate electrode 13 disposed therebetween.

A substantially U-shaped resistor track 15 is next deposited on the substrate such that the ends of the track contact the electrodes 12 and 14 respectively with the elongate electrode 13 being disposed between but spaced from the two limbs of the U. This resistor track may be applied by the conventional technique of printing the track with a conductive ink, deposited through an in-contact mask, followed by firing of the ink. Such techniques are well known in the art and need not be further described.

The structure is next overlaid with an ion-plated film 16 of a semiconductive metal oxide deposited from a radio frequency plasma containing the metal in vapour form together with an excess of an oxidizing vapour and optionally one or more depants for controlling the electrical characteristics of the film 16. The active region of the device is provided by the portion of the film 16 disposed between the elongate electrode 13 and the U-shaped resistor track 15. Preferably the film 16 comprises tin oxide doped with alumina and provided by electron bombarding a 0.1% aluminium alloy of tin into a radio-frequency oxygen plasma discharge. The tin and the aluminium are oxidized in the plasma and so form a layer of doped tin oxide on any solid surface exposed to the plasma. Such a film has been found to be highly specific to hydrogen sulphide.

In a preferred construction the reverse face of the substrate 11 is coated with a layer of gold formed e.g. by painting or printing with a gold ink followed by firing at 850° C. in air for about 10 minutes. This layer allows the substrate to be soldered to the surface of a suitable holder such as a dual-in-line (DIL) circuit package 17. The electrodes 12, 13 and 14 of the device can then be coupled to respective output pins 18 via ultrasonically bonded contact wires 19.

Figure 3:
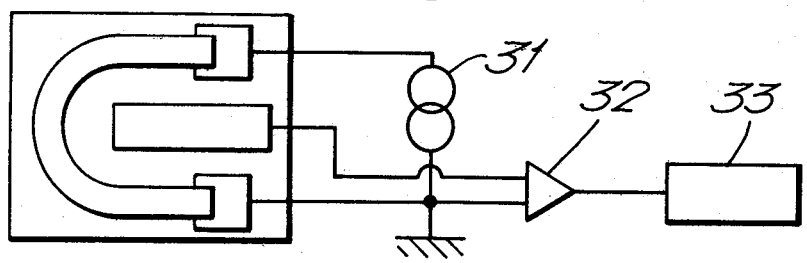
FIG. 3 is a block diagram of a gas measurement circuit incorporating the sensor of FIGS. 1 and 2.

In use a steady current is passed from a constant current source 31 (FIG. 3) through the resistor track via the electrodes 12 and 14 so as to maintain the device, and hence the metal oxide film 16, at an elevated temperature. Typically the current is controlled so as to maintain the device at 280° C. as it has been found that at this temperature the device has a fast response time and has a high selectivity to hydrogen sulphide gas. The resistance of the metal oxide film between the elongate electrode 13 and the resistor track is monitored via an amplifier 32 coupled to an output/display device 33. Exposure of the detector to the gas, e.g. hydrogen sulphide, causes a drop in the resistance of the metal oxide film, this resistance drop being a function of the gas concentration.

Figure 4:
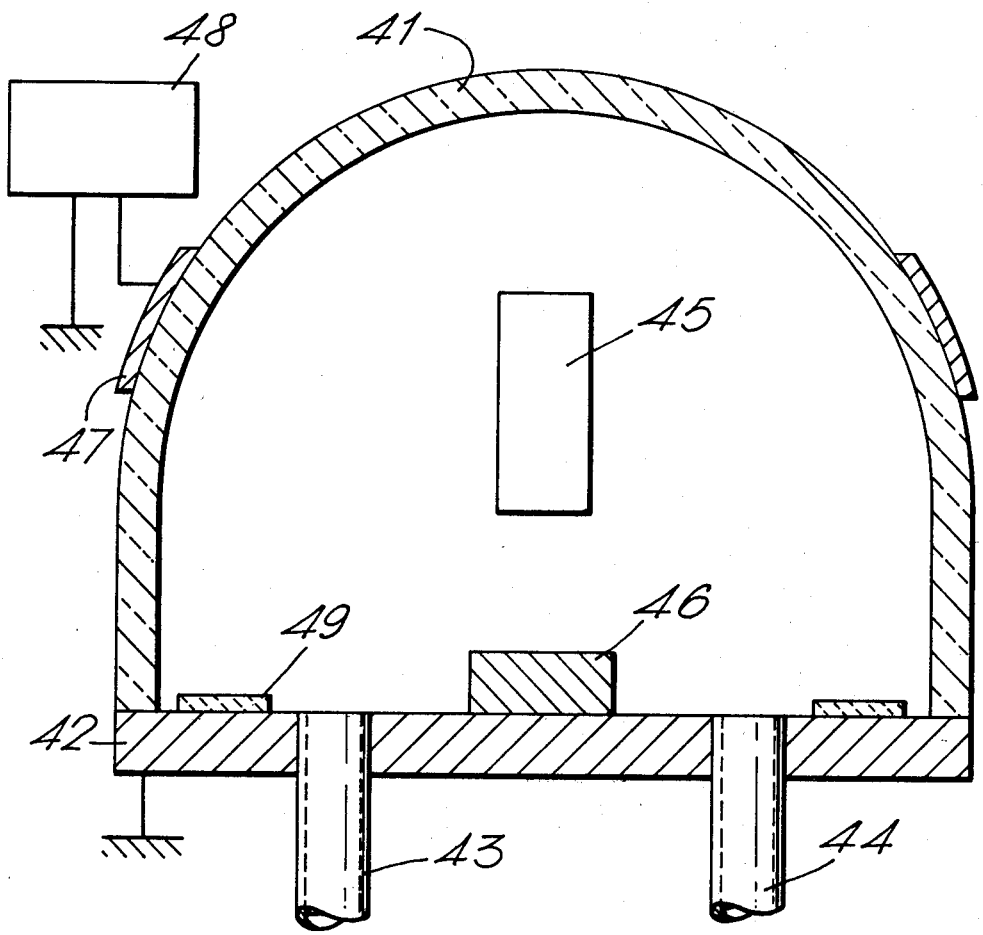
FIG. 4 is a schematic diagram of an ion-plating apparatus for fabricating the device of FIGS. 1 and 2.

An apparatus for ion-plating the metal oxide film is shown in FIG. 4 of the accompanying drawings. The apparatus includes a vacuum chamber defined by a glass bell jar 41 supported on a metal base plate 42. The chamber is evacuated via pipe 43 and reactant gases are supplied to the chamber via pipe 44. An electron gun 45 is mounted within the chamber and is directed towards a body 46 of the metal whose oxide is to be deposited. Typically this metal body 46 comprises a 0.1% aluminium tin alloy. Radio-frequency energy is supplied via electrode 47 from a generator 48.

To deposit the oxide film the chamber is evacuated and back filled with oxygen at a reduced pressure. The generator 48 is switched on to initiate a glow discharge or plasma into which the metal is then electron beam evaporated from the body 46. The metal vapour reacts with the oxygen plasma and a film of oxide is deposited on a plurality of workpieces 49 disposed radially around the metal body. We have found that to prevent the risk of deposition of unoxidized metal the workpieces 49 should be at least 50 mm from the metal body and in positions that are not in a line of sight with the electron beam target region. Typically we employ a 70 ma electron beam current together with an oxygen pressure of $10^{-5}$ torr for a period of 20 min. This gives a film thickness of 1,000 to 3,000 Å.

Figure 5A:
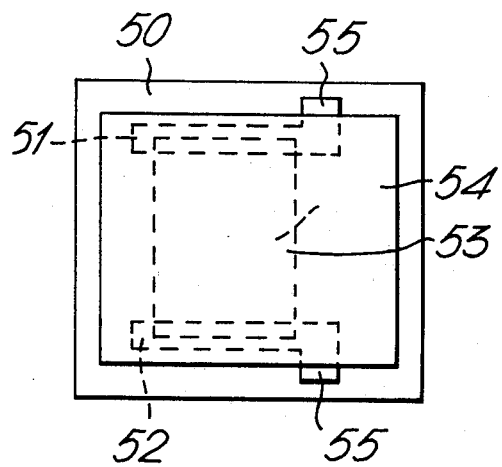
FIGS. 5a and 5b show, in plan views, successive stages in the manufacture of a second embodiment of semiconductor gas sensor device.
Figure 5B:
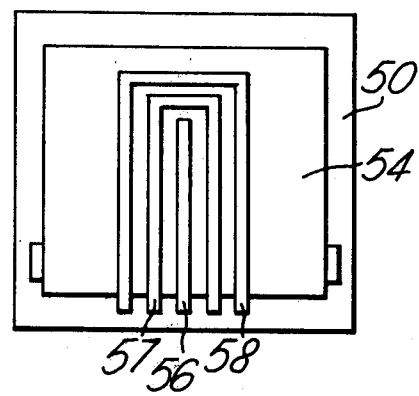

The embodiment of FIGS. 5a and 5b employs a different heater structure to that employed in the FIGS. 1 and 2 embodiment. The semiconductor gas sensor includes an insulating, typically alumina, substrate 50 on which two precious metal electrodes 51 and 52 are deposited. Typically the electrodes are of gold applied by means of a thick film ink deposition followed by firing. A heater strip 53 formed, for example, from Dupont 1411 thick film ink, is deposited on the substrate 50 such that opposite ends thereof contact the electrodes 51 and 52 respectively and subsequently fired. A dielectric glass layer 54 is then applied by thick film techniques to cover the heater strip 53 and the electrodes apart from contact pad areas 55 thereof and subsequently fired. An array of electrodes 56, 57, 58 are then applied on the dielectric film 54 to extend over the heater strip 53. Typically these electrodes are of gold and are provided by a conventional thick film technique and subsequent firing.

The centre electrode 56 is equivalent to the elongate electrode 13 of FIG. 1, the intermediate electrode 57 is equivalent to the resistor track 15 of FIG. 1 for the purposes of measuring the resistance of the metal oxide film between the centre electrode 56 and the intermediate electrode. The outer electrode 58 comprises a guard electrode for screening purposes.

Preferably the reverse face of the substrate 50 is coated with a layer of gold, as described with reference to substrate 11, to facilitate soldering to the surface of a suitable holder. After mounting to such a holder the electrodes 51, 52, 56, 57 and 58 are electrically connected to respective output pins by suitable connection wire techniques.

An ion-plated film (reference numeral 60 in the FIG. 6 variation of FIGS. 5a and 5b) of a semiconductor metal oxide, such as alumina doped tin oxide, is then deposited by the process described above to cover all exposed regions of the substrate and the various layers thereon. Alternatively the sensor film 60 may be deposited prior to mounting of the substrate on a holder, and attachment of the interconnection wires, in which case the film 60 would be deposited through a suitable mask so that the wire connection etc., can be performed subsequently to portions of the electrodes not coated with the sensor film.

Figure 6:
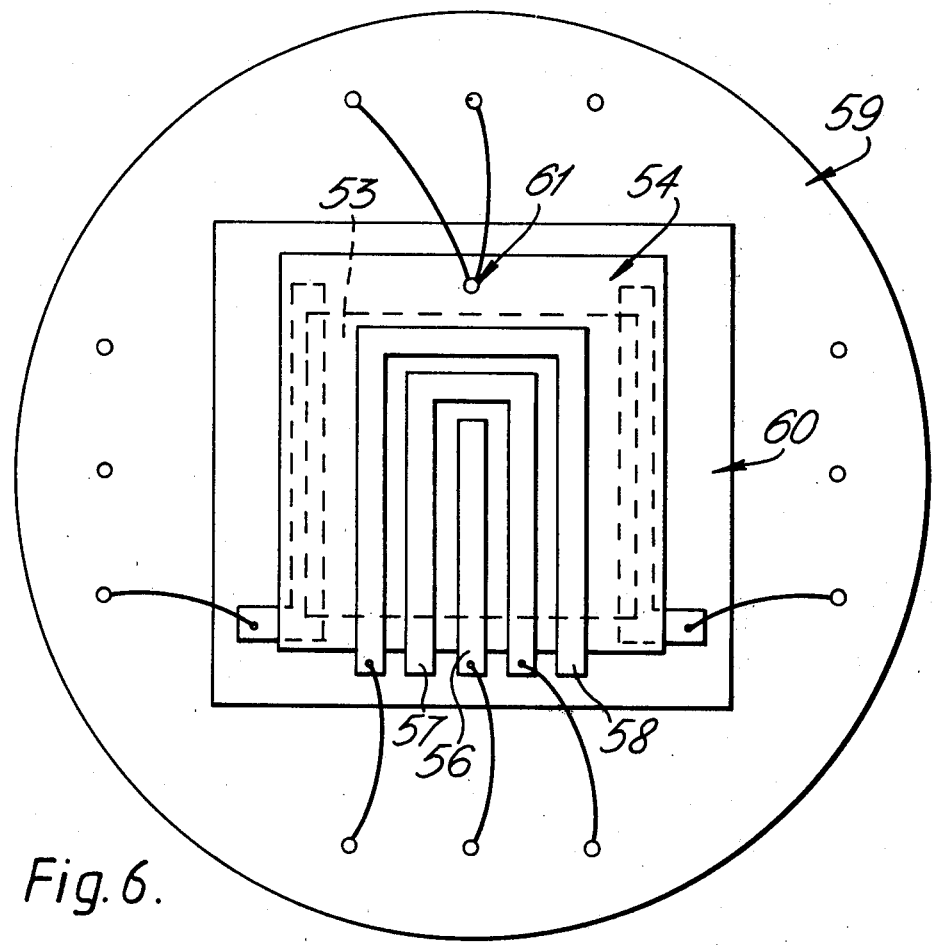
FIG. 6 shows a variation of the embodiment of FIGS. 5a and 5b as mounted on a 12 pin TO8 header.

In the FIG. 6 variation of the FIGS. 5a and 5b embodiments, the electrodes 56, 57 and 58 are orientated at 90° to those shown in FIG. 5b in order to facilitate mounting to a 12 pin TO8 header 59. The embodiment of FIG. 6 also includes a thermistor 61. Typically the thermistor 61 is a micro bead thermistor mounted on the surface of the device by melting the lead glass bead thereof into part of the thick film dielectric glass coating 54. The thermistor is employed for temperature control purposes so that the device can be operated accurately at ambient temperatures varying from −20° to +30° C. The thermistor comprises the control sensor for a heater power supply circuit (not shown in FIG. 6).

The use of the isolated (under dielectric) low resistivity, typically 10Ω, heater allows uniform heating of the sensor film to be obtained at low voltage and with low power consumption. At 20° ambient temperature 4 watts at 6 volts enables a 280° C. operating temperature to be achieved, in comparison with 4 watts at 12 volts for a device of the FIG. 1 construction, which requires a drop of 12 volts across the heater to obtain a 280° operating temperature and a further 12 volts to the measuring electrode. Thus battery powered sensors can be employed, which are of particular relevance to the use of sensors in potentially flammable atmospheres and/or in remote locations.

The isolating thick film dielectric layer 54 covering the film heater 53 provides a more uniform surface for the sensor film 60 to be deposited on than the alumina substrate of the FIG. 1 embodiment and this allows thinner sensor films, typically less than 500 Å (50 nm) to be deposited with good adhesion, continuity and stable resistivity in dry air.

The geometry of the thick film gold electrodes allows easily measurable electrical currents to flow from a low voltage source across 50 nm sensor films of 1 to 10 ohm cm resistivity. Typically the sensor resistances are 10 Mohms or less at 280° C. in dry air, falling to 0.5 Mohms or less when exposed to 10 ppm of hydrogen sulphide.

Ion-plating of doped tin oxide on a cold substrate provides a sensor film of controlled discontinuity. Low surface temperatures reduce the surface kinetic energy of the adhering atoms and/or radicals which minimises surface mobility and results in a maximum number of localised surface discontinuities. Thus choice of the surface temperature during film deposition optimises the concentration of surface sites for gas absorption and reaction without impairing the stability of the sensor resistance.

The ion-plated sensors described above show excellent sensitivity to hydrogen sulphide at temperatures as high as 280° C. The response to sulphur dioxide is generally 1000 times less, and the relative sensitivity to hydrogen is 1000 times less than for hydrogen sulphide.

The fastest response to and recovery from hydrogen sulphide exposure is obtained at temperatures of the order of 280° C. As the operating temperature of the sensor film is reduced, sensitivity, response and recovery are increasingly impaired. The evaporation of a thin layer of platinum on the surface of the sensor greatly improves the recovery of the device at lower temperatures. However, high temperature operation is preferred since this is considered to minimise the affect of absorbed moisture on the sensor devices.

At temperatures higher than 280° C. the sensor becomes more sensitive to other sulphur compounds, for example sulphur dioxide, so that in the absence of hydrogen sulphide and at 350° C., for example, reasonable selectivity to these other sulphur compounds can be obtained in the presence of flammable gases such as hydrogen, carbon monixide, methane and other hydrocarbons.

The following example illustrates the invention.

Using the apparatus of FIG. 4 a plurality of devices having the structure shown in FIGS. 1 and 2 (device Nos. A2 to B6) or the structure shown in FIG. 6 (device Nos. C1 to C5) were fabricated. Each device was electrically heated to a temperature of 280° C. and its film resistance measured in air (Ro) and in an air atmosphere containing 10 parts per million of hydrogen sulphide (R10). The results are summarised in the following table.

($t_{res}$ is the time taken for the initial resistance (Ro) to be halved (values taken to nearest 0.1 of a minute) when exposed to 10 ppm of $H_2S$.)

| Device No. | Film Thickness in Å | Ro (MΩ) | R10 (MΩ) | Ro/R10 | R10 resistivity in Ω cm$^{-1}$ | $t_{res}$ |
|---|---|---|---|---|---|---|
| A.2 | 2300–3000 | 0.022 | 0.0014 | 13.8 | 0.11 | 0.2 |
| A.3 | 2300–3000 | 0.025 | 0.0020 | 8.5 | 0.15 | 0.3 |
| A.4 | 2300–3000 | 0.175 | 0.0077 | 23.8 | 0.50 | 0.3 |
| A.5 | 2300–3000 | 0.291 | 0.0098 | 33.3 | 0.74 | 0.2 |
| A.6 | 2300–3000 | 0.203 | 0.0079 | 28.9 | 0.59 | 0.2 |
| B.1 | 1000–1200 | 0.074 | 0.0045 | 28.4 | 0.16 | 0.3 |
| B.2 | 1000–1200 | 0.090 | 0.0064 | 22.3 | 0.23 | 0.3 |
| B.3 | 1000–1200 | 0.053 | 0.0032 | 23.4 | 0.12 | 0.3 |
| B.4 | 1000–1200 | 0.063 | 0.0037 | 20.1 | 0.13 | 0.3 |
| B.5 | 1000–1200 | 0.020 | 0.0031 | 6.5 | 0.11 | 0.9 |
| B.6 | 1000–1200 | 0.020 | 0.0020 | 9.9 | 0.07 | 0.8 |
| C.1 | 500 | 6.8 | 0.31 | 22 | 6.2 | 0.2 |
| C.2 | 500 | 5.6 | 0.15 | 37 | 3.1 | 0.2 |
| C.3 | 500 | 6.0 | 0.20 | 30 | 4.1 | 0.2 |
| C.4 | 500 | 9.6 | 0.55 | 17 | 11.4 | 0.2 |
| C.5 | 500 | 4.5 | 0.18 | 25 | 3.9 | 0.2 |

These results illustrate the feasibility of producing gas sensor devices by the methods described herein.

Whilst the sensor devices described herein are specific to hydrogen sulphide at 280° C. it will be appreciated that specificity to other gases may be provided by using other temperatures or by ion-plating an appropriate semiconductive metal oxide to provide the active region.

I claim:

1. A hydrogen sulphide gas sensor comprising: a substrate insulator; first and second parallel conductive strips forming electrodes affixed to said substrate insulator in spaced relation to each other; a layer of a resistive heater material affixed to said substrate insulator and to said first and second strips; a dielectric film having obverse and reverse sides, said dielectric film having said reverse side thereof covering and fixed relative to said resistive heater material; third and fourth conductive strips forming electrodes, said third and fourth conductive strips being fixed to the obverse side of said dielectric film, said third and fourth conductive strips being long and thin in comparison to their widths, said third conductive strip being straight, said fourth conductive strip being U-shaped and straddling said third conductive strip, said fourth conductive strip having one leg on each side of and parallel to said third conductive strip, said legs being connected by a bight portion, each of said legs being uniformly spaced from said third conductive strip; and a semiconductive film fixed to said dielectric film between and in contact with said third and fourth conductive strips in a position to be heated by said heater means, said semiconductive film having a resistivity which decreases with an increase of hydrogen sulphide concentration in a gas contacting the same, said semiconductive film comprising tin oxide doped with alumina.

2. The invention as defined in claim 1, wherein a fifth conductive strip is affixed to said dielectric film, said fifth conductive strip being U-shaped and surrounding said fourth conductive strip.

3. A gas sensor comprising: a substrate insulator; a dielectric film having obverse and reverse sides; heater means fixed relative to and on said reverse side to supply heat to the vicinity of said obverse side; first and second conductive strips forming electrodes, said first and second conductive strips being fixed to the obverse side of said dielectric film, said first and second conductive strips being long and thin in comparison to their widths, said first conductive strip being straight, said second conductive strip being U-shaped and straddling said third conductive strip, said second conductive strip having one leg on each side of said first conductive strip, said legs being connected by a bight portion, each of said legs being uniformly spaced from said third conductive strip; and a semiconductive film fixed to said dielectric film between and in contact with said first and second conductive strips in a position to be heated by said heater means, said semiconductive film having a resistivity which decreases with an increase of hydrogen sulphide concentration in a gas contacting the same.

* * * * *